United States Patent
Stephenson et al.

(10) Patent No.: US 6,379,343 B2
(45) Date of Patent: *Apr. 30, 2002

(54) INFANT DIAPER CHANGING SHIELD

(75) Inventors: James R. Stephenson, Madison; Larry N. Brunette, McFarland, both of WI (US)

(73) Assignee: Miljarry, LLC, Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/473,231

(22) Filed: Dec. 27, 1999

(51) Int. Cl.$^7$ .................................................. A61F 5/44
(52) U.S. Cl. ........................ 604/349; 604/327; 604/346; 604/347; 604/351; 604/353
(58) Field of Search ........................ 2/49.1, 49.2, 49.3, 2/49.4, 49.5, 48, 52; 433/137; D2/861; 604/327, 346, 347, 348, 349, 351, 353, 356, 544, 674

(56) References Cited

U.S. PATENT DOCUMENTS

| | | | |
|---|---|---|---|
| 2,484,356 A | | 10/1949 | Ribeiro et al. |
| 2,525,115 A | * | 10/1950 | Britton .......................... 2/49.3 |
| 2,955,292 A | * | 10/1960 | McKend ........................... 2/48 |
| 3,182,661 A | | 5/1965 | Ribeiro et al. |
| 3,368,561 A | | 2/1968 | Ericson et al. |
| 3,406,690 A | | 10/1968 | Igel et al. |
| 3,741,203 A | * | 6/1973 | Liman ........................... 602/3 |
| 4,453,938 A | | 6/1984 | Brendling |
| 4,813,949 A | * | 3/1989 | O'Rourke .................... 604/391 |
| 5,107,545 A | * | 4/1992 | Potter .............................. 2/46 |
| 5,135,522 A | | 8/1992 | Fahrenkrug et al. |
| 5,346,483 A | | 9/1994 | Thaxton, Sr. |
| 5,490,289 A | * | 2/1996 | Lehrer ........................... 2/49.2 |
| 5,618,279 A | | 4/1997 | Pudio |
| 6,080,139 A | * | 6/2000 | Gallegos ...................... 604/387 |

* cited by examiner

Primary Examiner—John G. Weiss
Assistant Examiner—Michele Kidwell
(74) Attorney, Agent, or Firm—Lathrop & Clark LLP

(57) ABSTRACT

The people and things in the vicinity of an undiapered baby are protected from being urinated upon by a device which has an open resilient foam band, which is "C" or horseshoe shaped. The band has a curved front segment with two rearwardly extending side segments which allow the band to be resiliently clasped about the midsection of an infant. A urine receiving pad is connected to the front segment of the band, and extends downwardly to space a quantity of absorbent material from the infant. The pad has an exterior fluid impervious barrier to which a cotton or synthetic absorbent material is attached. The lower corners of the pad are turned up to define an upwardly opening pocket which better retains liquid. The shield is readily affixed to the infant prior to removal of the diaper, and throughout the period during which urination of the undiapered infant is likely. The pad may be constructed with a stiff paper card therein to retain the pad in a position elevated from the infant to keep the soiled absorbent material out of contact with the infant. In an alternative embodiment the absorbent pad may be provided separately from the band, and may be attached to the band by strips of hook and loop fasteners. The pads may then be disposed of after use, while the resilient band may be used many times.

1 Claim, 2 Drawing Sheets

INFANT DIAPER CHANGING SHIELD

CROSS REFERENCES TO RELATED APPLICATIONS

STATEMENT AS TO RIGHTS TO INVENTIONS MADE UNDER FEDERALLY SPONSORED RESEARCH AND DEVELOPMENT

BACKGROUND OF THE INVENTION

The present invention relates to infant hygiene products in general, and to devices for controlling the disposition of infant urine in particular.

Newborn babies and infants are not able to control urination. For this reason, from birth to several years of age, children are provided with diapers which serve to protect the child's surroundings from becoming soiled. However, once a diaper has been soiled, it must be removed from the infant and replaced with a fresh one. Yet, any time at which the infant is without a diaper is a time at which the infant's caregiver or surroundings are liable to be urinated upon. The flowable nature of urine is such that a very small quantity can cover significant surface area, and the pungent odor of the substance requires that urine on furniture, walls, and clothing be immediately and thoroughly cleaned up. The likelihood of this unrestricted urination is particularly increased at times when the child is without a diaper and is subject to sudden temperature changes, for example, when the insulating diaper is removed in cool air, or when the unclothed infant is placed in warm bath water.

Some experienced diaper changers have developed the ability to immediately substitute a fresh diaper the instant the soiled diaper is removed. With adequate manual dexterity and timing, this technique will protect both the diaper changer and surroundings from urine. Nevertheless, if successful, this approach results in a second diaper which is soiled before it has even reached the infant. Moreover, the protective backup diaper technique is more difficult to practice in situations where the unclothed infant is being transported, such as to the tub, or in the doctor's office.

What is needed is a low-cost, convenient, and easy to use device which protects the surroundings of the un-diapered infant from contamination by urine.

SUMMARY OF THE INVENTION

The infant diaper changing shield of this invention has an open resilient band, preferably made of foam, which is in the shape of the letter "C" or a horseshoe. The band has a curved front segment with two rearwardly extending side segments which allow the band to be resiliently clasped about the midsection or abdomen of an infant. A urine receiving pad has an upper margin which is connected to the front segment of the band. The pad extends downwardly from the band and is provided with a quantity of absorbent material which faces the infant. The pad may be formed with an exterior fluid barrier of a plastic material which is impervious to the flow of urine through it, and to which a cotton or synthetic absorbent material is attached. The lower corners of the pad are turned up to define an upwardly opening pocket which better retains liquid. The shield is readily affixed to the infant prior to removal of the diaper, and throughout the period during which urination of the un-diapered infant is likely. The pad may be constructed with a stiff paper card therein to retain the pad in a position elevated from the infant to keep the soiled absorbent material out of contact with the infant.

In an alternative embodiment, the absorbent pad may be provided separately from the band, and may be attached to the band by strips of hook and loop fasteners. The pads may then be disposed of after use, while the resilient band may be used many times.

It is object of the present invention to provide a device which minimizes the likelihood of a baby urinating on himself, the diaper changer, the changing station, home fixtures, walls, furniture etc.

It is another object of the present invention to provide an aid to diaper changing which reduces time lost to cleaning up infant urine.

It is also an object of the present invention to provide a low-cost short-term receptacle for infant urine during those times when the child is un-diapered.

It is a further object of the present invention to provide an aid to diaper changing which is readily employed by inexperienced persons to protect themselves from being urinated upon.

It is an additional object of the present invention to provide a device which temporarily remains in place upon a transported un-diapered baby and prevents the escape of urine onto the child's surroundings.

It is yet another object of the present invention to provide a urine protective shield for infant use which may be applied with one hand.

Further objects, features and advantages of the invention will be apparent from the following detailed description when taken in conjunction with the accompanying drawings.

DESCRIPTION OF THE PREFERRED EMBODIMENTS

Figure 1:
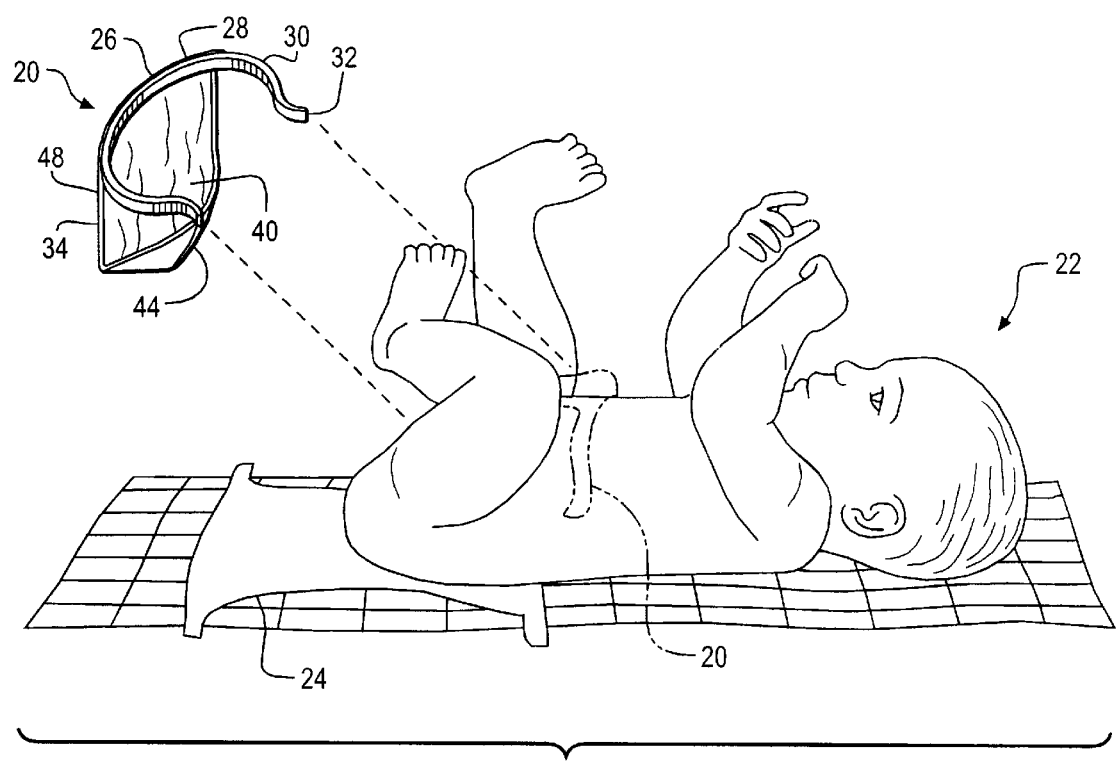
FIG. 1 is a perspective view of the diaper changing shield of this invention, shown in exploded view from its operational position.
Figure 2:
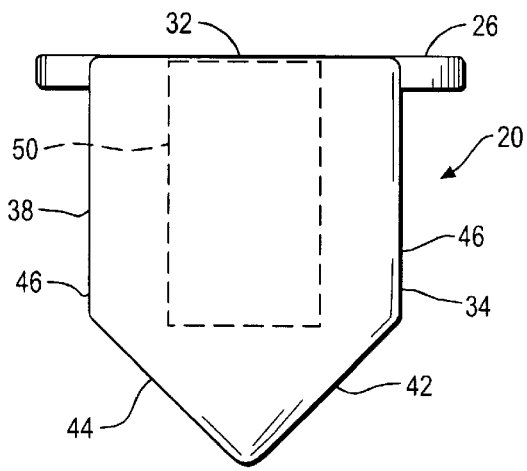
FIG. 2 is a front elevational view of the shield of FIG. 1.
Figure 3:
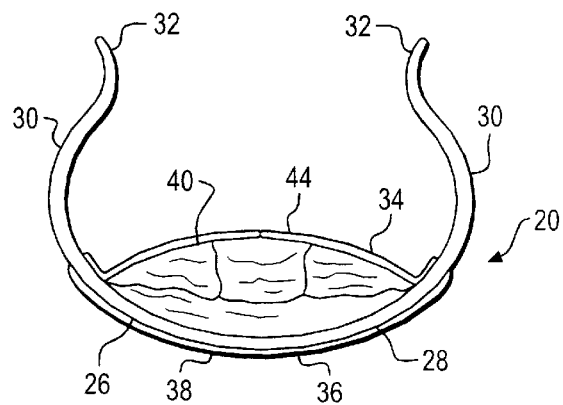
FIG. 3 is a top plan view of the shield of FIG. 1.

Referring more particularly to FIGS. 1–4, wherein like numbers refer to similar parts, an infant diaper changing shield 20 is shown in FIG. 1 in relation to an infant 22 requiring a fresh diaper 24. As shown in FIG. 3, the shield 20 has a resilient band 26 formed of a flexible material, such as a soft foam. Although flexible, the band 26 is springy, and will not typically be permanently deformed by deflections involved in ordinary use. The band has an open curved shape, generally similar to the letter "C" or to the shape of a horseshoe. The band 26 has a curved front segment 28 which is configured to generally match the curve of the infant's belly at about naval level. This front segment 28 has a diameter of about 4–6 inches, to generally accommodate infants 0–6 months old. Side segments 30 extend rearwardly from the front segment 28, and are each terminated by outwardly inclined tabs 32. The tabs 32 extend outwardly about ¾ inches and serve as ramps or guides which direct the band into position on the infant.

A urine receiving pad 34, as shown in FIG. 2, has an upper margin 36 which is connected to the band 26. The pad 34 may be fixed to the band 26 by an adhesive, such as hotmelt or pressure sensitive adhesive, by sonic welding or thermal bonding, by stitching, by mechanical fasteners, or a combination of these approaches or in any conventional fashion. The pad 34 has an outwardly facing fluid barrier 38 which is substantially impervious to the flow of urine therethrough. The pad fluid barrier 38 may be formed of a sheet of plastic material, for example a thin polyethylene film. As shown in FIG. 1, the pad 34 has absorbent portions 40 affixed to the barrier 38. The fluid barrier 38 and absorbent portions 40 may be constructed in a fashion similar to that employed in conventional diapers, for example HUGGIES® diapers manufactured by Kimberly-Clark Corporation, of Dallas, Tex.; or PAMPERS® diapers manufactured by The Procter & Gamble Company, of Cincinnati, Ohio. The absorbent portions 40 of the pad 34 may have a matrix of hydrophilic fibers, for example, a web of cellulosic fluff, such as wood pulp fluff, synthetic, polymeric, or meltblown fibers or natural fibers. These fibers may be mixed with particles of a high-absorbency material commonly known as superabsorbent material. Although other fluid retaining layers such as are employed in diapers may be used, such as a hydrophilic tissue wrapsheet, the urine receiving pad 34 does not have to meet the stringent demands placed on a diaper, as the pad 34 generally does not contact the skin of an infant 22 and is only momentarily mounted to the child.

The pad 34 may be constructed from a substantially rectangular sheet of plastic material comprising the fluid barrier 38, with a substantially rectangular wad of absorbent material comprising the absorbent portions 40 and disposed on the fluid barrier 38. At the lower margin 42 of the pad 34, the corners are turned up and joined to define a pocket 44. This pocket serves to restrict leaking from the absorbent portions 40, and also temporarily retains fluid as it is absorbed into the absorbent portions. Along the upwardly extending sides 46 of the pad 34, the fluid barrier 38 is turned inwardly over the absorbent portions 40 to define a hem 48. The shield 20 may be manufactured in a variety of sizes for use with infants of different ages and weights. One general purpose pad 34 is about 3½ inches wide, about five inches tall, and about 1 and ¼ inch deep at the pocket 44. The absorbent portions 40 may be about ½ inches thick. To give the pad 34 some stiffness, and to help in retaining the pad out of contact with the infant's skin, a paperboard card 50, approximately 2¾ inches tall and 2 inches wide is positioned between the fluid barrier 38 and the absorbent portions 40, extending downwardly from the upper margin 36, as shown in FIG. 2.

The use of the shield 20 may be understood with reference to FIG. 1. Whenever it is desired to temporarily remove the diaper 24 of the infant 22, either for the purpose of changing a soiled diaper, bathing the infant, examining the infant at the doctor's office or performing a medical procedure, the shield 20 is first pressed into place on the infant's abdomen, approximately at the level of the naval. The band 26 is small enough that it is readily clasped in one hand between the thumb and forefinger and is pressed on to the infant above the diaper 24. As the tabs 32 of the band side segments 30 engage the infant, they serve to spread the side segments so that the band passes over the front of the infant, bending resiliently, and thus attaching the shield 20 to the infant. Because of the foam construction of the band 26, very minimal pressure is supplied to the infant by this operation. Furthermore, the band 26 preferably has a very smooth and slick inwardly facing surface which glides over the infant's skin as the band is put in place. Because the band does not encircle the infant, there is no need to make any connection between parts of the bend, or even to lift the infant from its supporting surface. This one-handed application makes it possible to keep one hand free for supporting the infant.

Once attached, the band 26 supports the pad 34 in a position spaced slightly from the infant, thereby allowing the soiled diaper to be removed with the shield 20 in place. Generally, if urination is to occur, it will take place shortly after the soiled diaper has been removed. The child may be placed on a fresh diaper, and the diaper positioned for attachment before the shield 20 is removed and the diaper connected to the infant. In the event that urination does take place, the soiled shield 20 is disposed of in the same manner as a soiled diaper would be disposed of. If no urination takes place, the shield 20 may be set aside and used again at a later time. Likewise, if the child is to be placed in warm bath water, the shield will remain attached until the infant has come into contact with the water, and the period of likely urination has passed.

The shield 20, although particularly effective for male infants, is also effective for female infants. The device addresses the problems of many parents of infants, in that the infant unclothed urination is unpredictable and a chore to clean up. The shield 20, by preventing most such accidents, saves time, is usable in many different situations, and is less costly then an additional diaper.

Figure 4:
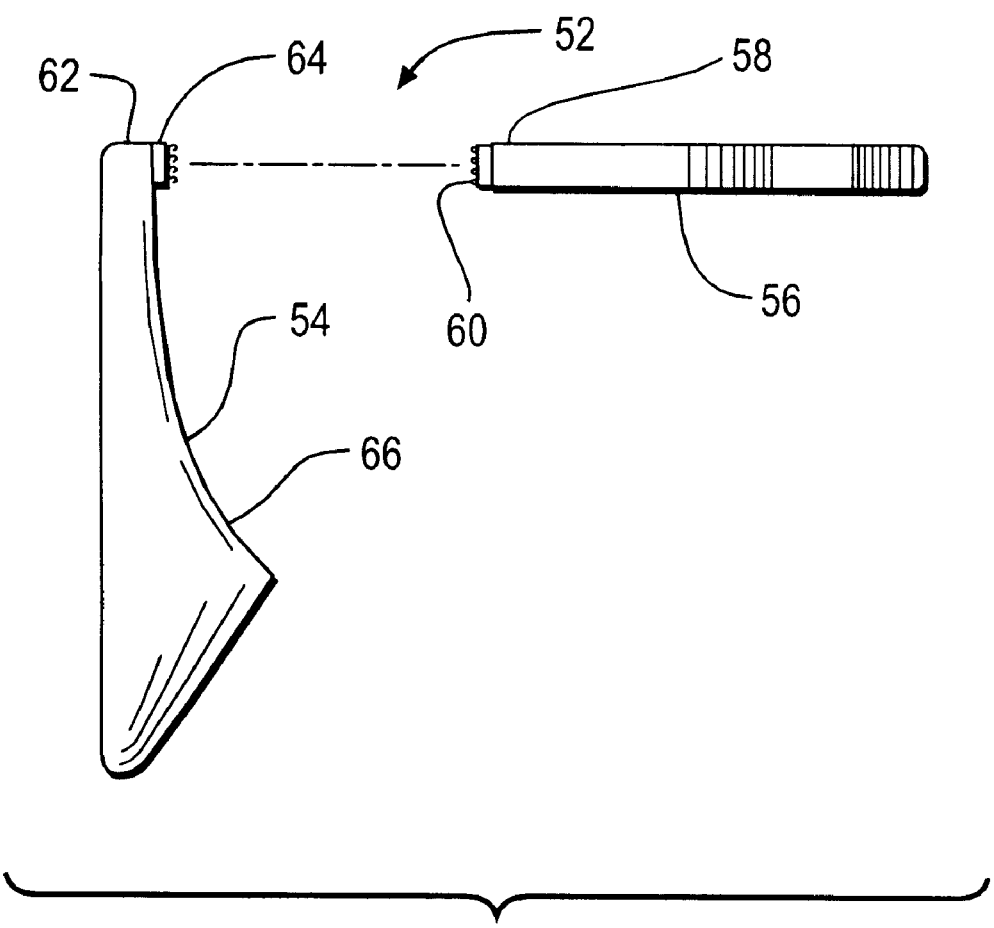
FIG. 4 is an exploded side elevational view of an alternative embodiment shield of this invention, having a replaceable absorbent pad.

An alternative embodiment changing shield 52 is shown in FIG. 4. The shield 52 is identical to the shield 20 discussed above, except that the urine receiving pad 54 with pocket 66 is a disposable unit which is separable from the band 56. The front segment 58 of the band 56 is provided with a strip 60 having one part of a hook and loop fastener, such as VELCRO® fastener, and the upper margin 62 of the pad 54 is provided with a strip 64 of the other part of the hook and loop fastener. The band 56 is thus reusable, while the pad 54 is discarded and replaced.

It should be noted that although the pad has been shown as generally rectangular, other shapes, including rounded or wedge shapes intended to better adapt to the anatomy of the infant may be constructed.

It is understood that the invention is not limited to the particular construction and arrangement of parts herein illustrated and described, but embraces such modified forms thereof as come within the scope of the following claims.

We claim:

1. A method for shielding an infant caregiver and surroundings from projected urine during changing an infant's diaper, comprising steps of:

bringing a resilient rearwardly opening band into engagement with an infant at a position near a waist of the infant, to thereby resiliently engage the resilient rearwardly opening band to the infant without encircling the infant, a urine receiving pad extending downwardly from the resilient rearwardly opening band and being positioned by the resilient rearwardly opening band at a location spaced from a source of urine;

leaving the resilient rearwardly opening band and urine receiving pad attached to the infant once a soiled diaper has been removed for a selected period of time for receiving therein any urine to be immediately projected from the source of urine;

applying a fresh diaper to the infant; and removing the resilient rearwardly opening band and urine receiving pad from the infant.

\* \* \* \* \*